United States Patent [19]

Dodd

[11] 4,264,449
[45] Apr. 28, 1981

[54] ANTIBODY-SPECIFIC SOLID PHASE IMMUNOADSORBENT, PREPARATION THEREOF, AND ANTIBODY PURIFICATION THEREWITH

[75] Inventor: Roger Y. Dodd, Bethesda, Md.

[73] Assignee: American National Red Cross, Washington, D.C.

[21] Appl. No.: 116,307

[22] Filed: Jan. 28, 1980

Related U.S. Application Data

[62] Division of Ser. No. 835,307, Sep. 21, 1977.

[51] Int. Cl.$^3$ ............................................. B01D 15/08
[52] U.S. Cl. .................................... 210/656; 210/927
[58] Field of Search .................. 210/31 C, 198 C, 502

[56] References Cited

U.S. PATENT DOCUMENTS

| | | | |
|---|---|---|---|
| 4,029,583 | 6/1977 | Chang et al. | 210/198 C |
| 4,111,838 | 9/1978 | Schaeffer | 210/31 C |
| 4,162,355 | 7/1979 | Tsibais | 210/31 C |

Primary Examiner—John Adee
Attorney, Agent, or Firm—Holman & Stern

[57] ABSTRACT

An antibody-specific solid phase immunoadsorbent is prepared by adsorptively binding a lipid-containing viral antigen, such as hepatitis B surface antigen, to the surface of a porous glass carrier having an average pore diameter within the range of about 40–200 nm and an adsorptive surface which within the pH range of 2–8 is capable of selectively and stably binding lipid-containing materials, employing an adsorption buffer having a pH within such range. The high adsorptive selectivity of the carrier surface for the antigen under such conditions, enables preparation of the immunoadsorbent directly from whole human plasma containing the antigen, without the necessity for prior antigen purification. The resultant immunoadsorbent has a high complexing specificity, efficiency and capacity for the specific antibody to the bound antigen, is capable of providing a reasonably high yield of the specific antibody, and is stable under the conditions required for antibody-antigen complexing and dissociation, thereby rendering it highly effective for the isolation and purification of the specific antibody by affinity chromatography techniques.

A specific application of the methods and materials described which is of particular clinical significance is in providing a relatively simple and inexpensive procedure for recovering purified hepatitis B antibody from standard immune serum globulin.

11 Claims, No Drawings

ANTIBODY-SPECIFIC SOLID PHASE IMMUNOADSORBENT, PREPARATION THEREOF, AND ANTIBODY PURIFICATION THEREWITH

This is a division of application Ser. No. 835,307, filed Sept. 21, 1977.

BACKGROUND OF THE INVENTION

This invention relates to antibody purification by affinity chromatography techniques and, more particularly, to antibody-specific solid phase immunoadsorbents for use therein.

Immune serum globulin (ISG), also referred to as gamma globulin, is a fraction of blood plasma which is rich in antibodies, and is commericially prepared from large pools of plasma by conventional fractionation techniques well known in the art. Many clinically important antibodies are present in immune serum globulin in varying concentrations. With respect to certain diseases, such as measles and infections (type A) hepatitis, the antibodies thereto are present in the immune serum globulin in sufficiently high concentrations so that the immune serum globulin as such is an effective prophylactic agent against these diseases. While other antibodies, such as antibody to serum (Type B) hepatitis, rubella and varicella-zoster viruses, are present in immune serum globulin, their concentration is generally too low for immune serum globulin to be prophylactically effective against these diseases. Moreover, normal immune serum globulin has generally not been regarded as an economically practical source for obtaining these low concentration antibodies in more purified form.

For prophylaxis against serum hepatitis and other diseases against which immune serum globulin is prophylactically ineffective, the current practice has been to prepare specific immune globulin by fractionating the blood of persons who have a large amount of the required antibody. Since such persons are not common, a large number of expensive screening tests must be performed to select the best donors. In the case of hepatitis B antibody, for example, only about 4% of blood donors have detectible levels, and tests may cost up to $1.50 per donor.

Among the various fractionation procedures which have previously been proposed for purification of specific antibodies is affinity chromatography, employing a solid phase immunoadsorbent comprising the antigen specific to the specific antibody bound to an insoluble carrier material. This technique involves the removal of the specific antibody from the starting solution thereof by selective complexing of the specific antibody with the antigen moiety of the immunoadsorbent, and subsequent elution of the specific antibody from the immunoadsorbent by dissociation of the antibody-antigen complex. While antibody purification by affinity chromatography has previously been employed in relatively small-scale operations with regard to antibodies primarily of laboratory interest, this technique has generally not been regarded as an economically practical means for relatively large-scale commercial preparation of clinically significant specific immune globulin, primarily due to the expense and difficulties involved in the preparation of suitable immunoadsorbents.

In order to be practical for use in large-scale antibody purification, an immunoadsorbent should meet certain basic requirements. First of all, it must be stable under the conditions required for antibody-antigen complexing and dissociation, so that under such conditions the antigen moiety of the immunoadsorbent will not be released from the carrier surface. Secondly, it should have a high complexing specificity for the specific antibody being purified, so as to minimize the amount of nonspecific protein carried over into the purified product. Thirdly, it should have a high complexing efficiency for the specific antibody, i.e., it should be capable of complexing a high percentage of the total specific antibody applied thereto. Fourthly, it should have a reasonably high complexing capacity for the specific antibody, i.e., it should be capable of complexing a reasonably high amount of specific antibody per unit weight of immunoadsorbent. Additionally, it should be capable of providing a reasonably high yield of the specific antibody, i.e., the percentage of the complexed antibody that is released from the immunoadsorbent during elution, since this determines the number of complexing sites available on the immunoadsorbent for reuse and hence the life span of the immunoadsorbent.

The major obstacles to economically preparing immunoadsorbents meeting the above criteria have been the difficulties and expense involved in effectively, selectively and stably binding to the carrier surface sufficient amounts of the particular antigen specific to the specific antibody to be purified. The surfaces of the carrier materials typically employed for this purpose generally do not possess the requisite combination of high binding affinity, selectivity and capacity for the particular antigen to be bound. For this reason, immunoadsorbent preparation has generally required the rather expensive and time-consuming procedure of first chemically reacting the carrier surface with an intermediate coupling agent to increase its binding affinity for the antigen, purifying the antigen to compensate for the non-selectivity of the carrier surface and thereby reduce nonspecific binding, and thereafter chemically coupling the purified antigen to the carrier surface through the intermediate coupling agent.

The insoluble carrier materials which have previously been employed for preparing immunoadsorbents include both organic polymeric materials and various inorganic materials, such as glass, which is particularly advantageous since it is dimensionally stable and can be thoroughly cleaned to remove contaminants, for example, by sterilization. The use of porous glass as a carrier material is disclosed, for example, in the Weetall U.S. Pat. No. 3,652,761, issued Mar. 28, 1972, but no particular significance is attached to the particular pore size of the porous glass. Furthermore, Weetall's method of preparing immunoadsorbents requires the use of an intermediate silane coupling agent to effect adequate bonding between the surface of the glass carrier and the particular antigens contemplated. Moreover, while it is known that certain biological materials, particularly those containing lipids, will adhere to normal glass surfaces under acidic conditions and will be released therefrom under strongly basic conditions, and that it is possible by techniques based on this principle to achieve at least some degree of purification of certain lipid-containing viral antigens, such as hepatitis B surface antigen, this principle does not appear to have been previously applied to the preparation of solid phase affinity chromatography immunoadsorbents which could successfully be used to achieve significant degrees of antibody purification.

SUMMARY OF THE INVENTION

It is, accordingly, a primary object of the present invention to provide a relatively simple and inexpensive method for antibody purification by affinity chromatography, which can be used for the economical purification of certain clinically important antibodies, particularly hepatitis B antibody.

Another object of the invention is to provide a method in accordance with the preceding object, which can be used for extracting such antibodies from normal immune serum globulin.

A further object of the invention is to provide solid phase immunoadsorbents for use in the affinity chromatography method in accordance with the preceding objects, which have high complexing specificity, efficiency and capacity for the specific antibody to be purified, which are capable of providing a reasonably high yield of the specific antibody, and which are highly stable under the conditions required for antibody-antigen complexing and dissociation.

Still another object of the invention is to provide antibody-specific solid phase immunoadsorbents in accordance with the preceding object, whose preparation can be carried out relatively simply and economically, directly from whole human plasma containing the required antigen and without the necessity for prior antigen purification.

A still further object of the invention is to provide an antibody-specific solid phase immunoadsorbent in accordance with the preceding object, whose preparation does not require the use of an intermediate coupling agent for stable binding of large quantities of the specific antigen to the carrier surface.

The above and other objects are achieved in accordance with the present invention by providing an antibody-specific solid phase immunoadsorbent comprising a porous glass carrier having an average pore diameter within the range of about 40-200 nm and an adsorptive surface which within the pH range of about 2-8 is capable of selectively and stably binding lipid-containing materials, and a lipid-containing viral antigen, such as hepatitis B surface antigen, adsorptively bound to the carrier surface.

Preparation of such immunoadsorbent may be carried out directly from standard antigen preparations, such as whole human plasma containing the particular antigen, without the necessity of prior antigen preparation, and furthermore without the necessity of any intermediate coupling agent. The immunoadsorbent is prepared by first preparing a solution of the antigen preparation in an aqueous adsorption buffer having a pH within the range of about 2-8, and contacting the resulting antigen solution with the porous glass carrier so as to effect selective adsorptive binding of the lipid-containing viral antigen to the carrier surface. The carrier surface is thereafter washed with an aqueous washing liquid having a pH within the range of about 2-8, so as to effect removal from the carrier surface of any residual unbound material.

The resultant solid phase immunoadsorbent has a high complexing specificity, efficiency and capacity for the specific antibody to the bound antigen, is capable of providing a reasonably high yield of the specific antibody, and is highly stable under the conditions required for antibody-antigen complexing and dissociation, thereby rendering it highly effective for the isolation and purification by affinity chromatography techniques of the specific antibody from a preparation containing said antibody, including normal immune serum globulin. Antibody purification employing the immunoadsorbent of the present invention is carried out by first preparing a solution of the starting antibody preparation in a neutral pH isotonic complexing buffer, and contacting the resulting antibody solution with the immunoadsorbent so as to effect selective complexing of the specific antibody with the antigen moiety of the immunoadsorbent. The immunoadsorbent is then washed with an additional amount of the complexing buffer so as to effect removal therefrom of any residual uncomplexed material. Following the washing step, the specific antibody is then eluted from the immunoadsorbent with a suitable elution buffer capable of dissociating the complex of the specific antibody with the antigen moiety without effecting release of the antigen moiety from the carrier surface or destruction of the integrity of the eluted antibody.

DESCRIPTION OF PREFERRED EMBODIMENTS

The carrier material employed in preparing the solid phase immunoadsorbent in accordance with the present invention, is porous glass having an average pore diameter within the range of about 40-200 nm and an adsorptive surface which within the pH range of about 2-8 is capable of selectively and stably binding lipid-containing materials. Porous glass of this type is readily commercially available (for example, from Electronucleonics, Fairfield, N.J.), and can be prepared in accordance with the teachings of the Haller U.S. Pat. No. 3,549,524, issued Dec. 22, 1970).

The adsorptive surface characteristics specified for the porous glass carrier are very similar to those exhibited by normal glass surfaces, which are known to be slightly negatively charged. Surface modification of the porous glass, such as by treatment with the silane coupling agents specified in the Weetall U.S. Pat. No. 3,652,761, referred to above, reverses the surface charge of the glass from negative to positive, and thereby reduces the adsorptive affinity and selectivity of the glass surface for lipid-containing materials. Since the successful preparation and use of the immunoadsorbent in accordance with the present invention relies heavily upon the porous glass surface having a high binding affinity and selectivity for lipid-containing materials, it is therefore apparent that eliminating the use of such silane coupling agents not only is a time- and expense-saving advantage of the present invention, but indeed is an essential feature thereof.

The use of porous glass, as opposed to normal glass, as the carrier material, as well as the specified pore diameter of the porous glass, are also important features of the present invention. These features provide the carrier material with a sufficiently high antigen-binding capacity so that the resultant immunoadsorbent will have the requisite complexing efficiency and capacity for the specific antibody to the bound antigen so as to be economically practical and effective for antibody purification. The porous nature of the carrier material provides it with a relatively large surface area per unit of weight, which increases with decreasing pore diameter. The larger the surface area of the carrier material, the greater will be its potential for antigen binding during preparation of the immunoadsorbent and antibody complexing during its use, provided that the pore diameter is sufficiently large so as to allow free access of antigen and antibody. An average pore diameter within the range of about 40–200 nm provides the carrier material with suitable characteristics for suitable immunoadsorbent efficiency and capacity in regard to substantially all of the lipid-containing viral antigen-antibody systems of clinical importance, with the optimum pore diameter within such range for providing optimum immunoadsorbent efficiency and capacity varying with the particular system employed. For example, for the hepatitis B surface antigen-antibody system, optimum immunoadsorbent efficiency and capacity will generally be obtained when the porous glass carrier has an average pore diameter of about 150 nm.

The particular surface characteristics of the porous glass carrier material described above are utilized in accordance with the present invention for the simple and economical preparation of a wide variety of antibody-specific solid phase immunoadsorbents wherein the antigen moiety thereof may be any lipid-containing viral antigen. Such an immunoadsorbent in accordance with the present invention which is of particular clinical significance is one wherein the antigen moiety thereof is hepatitis B surface antigen. Other viruses whose antigens contain lipids include, for example, poliovirus, adenoviruses, vesicular exanthem virus, vaccinia virus, yellow fever virus, rabies virus, influenza and parainfluenza viruses, herpes viruses including varicella-zoster virus, mumps, measles and rubella viruses.

Preparation of the immunoadsorbent in accordance with the present invention is effected by adsorptively binding the lipid-containing viral antigen to the surface of the porous glass carrier, employing an aqueous adsorption buffer having a pH within the range of about 2–8. Suitable adsorption buffers include, for example, 0.1 M glycine-HCl buffer, pH 2–3; 0.1 M sodium citrate-HCl buffer, pH 4; and 0.067 M phosphate buffer, pH 6–8. The highly selective adsorptive affinity of the carrier surface for the antigen under such pH conditions, enables preparation of the immunoadsorbent directly from standard antigen preparations, such as whole human plasma containing the antigen, without the necessity for prior antigen purification.

Prior to its being contacted with the antigen preparation, the porous glass carrier is preferably subjected to a pretreatment with about one percent aqueous polyethylene glycol having an average molecular weight of about 4000 (PEG-4000), and vacuum is then applied to degas the glass surface. The PEG pretreatment appears to help to reduce nonspecific adsorption of proteins. The porous glass carrier is then washed several times with the adsorption buffer and allowed to equilibrate with the buffer.

The antigen preparation is preferably pretreated by over night dialysis against a large excess of the adsorption buffer. Following such dialysis, a solution is prepared of the antigen preparation in the adsorption buffer.

The resulting antigen solution is then contacted with the porous glass carrier so as to effect selective adsorptive binding of the antigen from the solution to the carrier surface. Appropriate adsorption conditions and relative amounts may vary somewhat depending upon the particular materials employed. For example, when binding hepatitis B surface antigen to a porous glass carrier having an average pore diameter of about 150 nm from an antigen solution comprising hepatitis B surface antigen-positive whole human plasma in an equal volume of 0.1 M glycine-HCl buffer, pH 3, gentle mixing of 2.0 ml of the antigen solution per 100 mg of the carrier for a period of at least about 4 hours has been found to be appropriate.

Following the adsorptive binding step, the carrier surface is washed with an aqueous washing liquid having a pH within the range of about 2–8, so as to effect removal from the carrier surface of any residual unbound material. The washing step is preferably carried out sequentially, first with additional amounts of the adsorption buffer previously used, then with distilled water, and finally with phosphate buffered saline, pH 7–7.2. While either batch or column procedures may be used for washing, it is preferred to carry out the adsorption buffer and distilled water washes in batch, and exhaustive washing with the phosphate buffered saline in a column.

If the final immunoadsorbent is to be used for the preparation of antibodies for clinical use, it will be necessary to insure that the antigen has been subjected to viral inactivation conditions. Viral inactivaton may be carried out by standard inactivation procedures either prior or subsequent to the binding of the antigen to the carrier material. For example, the starting plasma may be subjected to a heat pretreatment at about 60° C. for about sixteen hours. Alternatively, the bound antigen may be treated with formalin for about 96 hours at 37° C. subsequent to the washing step.

The resultant immunoadsorbent may then be used in affinity chromatography procedure for the isolation and purification of the specific antibody to the bound antigen from various preparations containing such specific antibody, such as, for example, whole human plasma, serum, or immune serum globulin. A solution is first prepared of the antibody preparation in a neutral pH isotonic complexing buffer, such as phosphate buffered saline, pH 7–7.2. The resulting antibody solution is then contacted with the immunoadsorbant so as to effect selective complexing of the specific antibody with the antigen moiety of the immunoadsorbent. Such contacting will generally be carried out in a column, particularly when relatively large volumes of antibody solution are employed, for example, greater than ten times the volume of the immunoadsorbent. For lesser volumes, batch procedures may be employed, with gentle mixing for approximately 2½ hours at room temperature generally being satisfactory. In column procedures, flow rates of antibody solution of up to 20 column volumes per hour will generally be suitable. Following the complexing step, the immunoadsorbent is then washed with an additional amount of the complexing buffer so as to effect removal therefrom of any residual uncomplexed material.

Elution of the complexed specific antibody from the immunoadsorbent may be effected with any suitable elution buffer capable of dissociating the specific antibody-antigen complex without effecting release of the antigen moiety from the carrier surface or destruction of the integrity of the eluted antibody. Since the adsorptive binding of the antigen moiety to the carrier surface is reliably stable only within the pH range of about 2–8, elution conditions outside of this range should be avoided. Additionally, elution conditions should be selected to give maximum yields with minimum effect on the integrity of the eluted antibody. Elution can generally be effectively carried out under conditions of either reduced pH or increase concentrations of chaotropic ions (typically, halides or thiocyanate), with the most effective elution buffer being dependent upon the particular antigen-antibody system being employed. For example, with the hepatitis B surface antigen-antibody system, low pH elution buffers, such as 0.1 M glycine-HCl buffer, pH 2.8, or 0.1 M citrate-HCl buffer, pH 2.8, and high chaotropic ion concentration buffers, such as 4 M sodium thiocyanate or 4 M potassium bromide, have been found to be suitable, with the citrate buffer or potassium bromide being particularly effective.

Dissociation of the antibody-antigen complex may be by means of a pH or concentration gradient or, preferably, by an abrupt step, since the latter procedure results in a sharper elution peak. The eluant is run through the column at room temperature at a suitable rate, for example, two column volumes per hour. The effluent is fractionated, dialyzed against phosphate-buffered saline, and protein and antibody content are monitored. Antibody-containing fractions may be pooled and concentrated or lyophilized.

Prior to the start of the affinity chromatography procedure, it is preferable, in order to minimize release of bound antigen during the elution step, to subject the immunoadsorbent to a pretreatment comprising a first prewash with a buffer of lower pH or higher chaotropic ion concentration, as the case may be, than the elution buffer to be employed. Thus, where the elution buffer to be employed is 0.1 M citrate-HCl buffer, pH 2.8, such prewash would be with a similar buffer of lower pH, for example, 0.1 M citrate-HCl buffer, pH 2.5; while where the elution buffer to be employed is 4 M potassium bromide, such prewash would be with a similar buffer of higher chaotropic ion concentration, for example, 4.5 M potassium bromide. In either case, such first prewash is followed with a subsequent prewash with the complexing buffer to be employed so as to return the immunoadsorbent to neutral pH and isotonic conditions.

When utilized in the above-described manner for antibody purification by affinity chromatography techniques, the solid phase immunoadsorbents of the present invention exhibit a high degree of stability and a high complexing specificity, efficiency and capacity for the specific antibody to the bound antigen, even from a preparation containing very low concentrations of the specific antibody. In addition, the immunoadsorbents are capable of providing a reasonably high yield of the specific antibody, thereby providing them with a good life span for subsequent reuse. These features, coupled with the fact that they may be simply and economically prepared directly from whole human plasma containing the required antigen without the necessity for prior antigen purification and without the necessity for prior carrier surface modification with an intermediate coupling agent, render the immunoadsorbents of the present invention particularly useful as a simple, effective and economical means for recovering purified clinically important antibodies, particularly hepatitis B antibody, from standard immune serum globulin, which is currently a product available in large excess and not previously regarded as an economically practical source for obtaining such purified antibodies.

For purpose of further illustrating the materials and methods of the present invention by way of a specific preferred embodiment thereof, the following examples describe the preparation of a hepatitis B antibody-specific solid phase immunoadsorbent in accordance with the present invention and its use in purifying hepatitis B antibody from normal immune serum globulin.

EXAMPLE 1

Immunoadsorbent Preparation

Ten grams of porous glass (CPG-1500, obtained from Biorad), 100-200 mesh, pore size 150 nm, were suspended in 100 ml of one percent polyethylene glycol 4000 in distilled water. A vacuum was applied for ten minutes in order to expell air. The porous glass was washed three times with 100 ml of 0.1 M glycine-HCl buffer, pH 3.0, and left overnight in the same buffer.

100 ml of a recalcified pool of whole human plasma containing hepatitis B surface antigen at levels detectible by counter-electrophoresis were dialysed overnight at 4° C. against one liter of 0.1 M glycine-HCl, pH 3.0. After dialysis, this plasma was diluted to 200 ml with the same buffer.

The porous glass was transferred in equal amounts into 50 ml serum bottles. The supernatant was removed and 40 ml of the buffer-diluted plasma were added to each bottle. The bottles were rotated gently, end over end, for five hours at room temperature. The supernatant was then decanted and the porous glass material in each bottle was similarly washed for ten minutes with 0.1 M glycine-HCl, pH 3.0. This step was repeated. The porous glass material was then pooled into a beaker and washed by stirring gently with 500 ml of distilled water for ten minutes. Three further washes were performed using phosphate buffered saline, pH 7.2. The porous glass material was then poured into a plastic chromatographic column, diameter 2.5 cm. The bed depth was 6 cm (column volume equals 30 ml). One liter of phosphate buffered saline, pH 7.2, was pumped through the column at 300 ml/hour to complete the washing. The column was then exposed to 0.1 M glycine-HCl buffer, pH 2.5, by pumping approximately 300 ml through the column at 60 ml/hour. This was followed by phosphate buffered saline, pH 7.2, thus returning the pH of the resultant solid phase immunoadsorbent to 7.2.

EXAMPLE 2

Antibody Purification 100 grams of normal immune serum globulin were dissolved in phosphate buffered saline, pH 7.2, to give a total volume of 2 liters. The solution was passed over the solid phase immunoadsorbent column prepared in Example 1, at 300 ml/hr (10 column volumes per hour). This use followed by one liter of phosphate buffered saline, pH 7.2, at the same rate.

Elution stages were performed at a flow rate of two column volumes per hour. 0.1 M glycine-HCl buffer, pH 2.8, was run into the column immediately following the phosphate buffered saline. The absorbance of the effluent and its pH were monitored and the effluent was fractionated. A protein peak emerged coincident with the change in pH of the effluent. The fractions constituting the peak were dialysed overnight at 0°-4° C. against phosphate buffered saline, pH 7.2.

A working estimate of protein content was obtained by determining absorbance at 280 nm and using the approximation: 1 mg/ml of protein has an absorbance of 1.0 in a 1 cm light path.

Anti-$HB_s$ (antibody to hepatitis B surface antigen) was measured by passive hemagglutination (PHA) and by a solid phase sandwich type radioimmunoassay (AusAB). The specificity of the antibody was assured by specific absorption of its activity with a known hepatitis B surface antigen specimen.

The specificity of antibody complexing on the immunoadsorbent was demonstrated by measuring antibodies to *Staphylococcus epidermidis* and *Escherichia coli* by a tube agglutination test. Specificity of these antibodies was demonstrated by absorption with homologous bacteria and lack of absorption with the heterologous organisms.

Immunoelectrophoretic analysis was performed upon concentrated fractions of the anti-HB$_s$-containing peak, the starting immune serum globulin and the immune serum globulin effluent from the column.

The results of the above tests indicated that all antibody to hepatitis B antigen was removed from the immune serum globulin by passage thereof through the column. Thirty percent of the antibody was recovered by elution in 0.03% of the starting protein; a purification of some 900-fold. Antibody to *Staphylococcus epidermidis*, present in the immune serum globulin starting material, was unchanged in the immune serum globulin effluent from the column, and was not recovered in the eluted final product. The eluted final product contained only IgG (i.e., immunoglobulin of the G class) when tested by immunoelectrophoresis.

By substituting for the glycine-HCl elution buffer either 0.1 M citrate-HCl buffer, pH 2.8, or 4 M potassium bromide, it has been found possible to achieve purification as high as 4000-fold with recoveries of up to 72 percent.

The embodiments of the invention in which an exclusive property or privilege is claimed are defined as follows:

1. An affinity chromatography method for the isolation and purification of a specific antibody from a preparation containing said antibody, comprising the steps of:
   (a) preparing a solution of said antibody preparation in a neutral pH isotonic complexing buffer;
   (b) contacting the resulting antibody solution with a solid phase immunoadsorbent comprising a porous glass carrier having an average pore diameter within the range of about 40–200 nm and an adsorptive surface which within the pH range of about 2–8 is capable of selectively and stably binding lipid-containing materials, and a lipid-containing viral antigen specific to said specific antibody adsorptively bound to said carrier surface, so as to effect selective complexing of said specific antibody with the antigen moiety of said immunoadsorbent;
   (c) washing said immunoadsorbent with an additional amount of said complexing buffer so as to effect removal therefrom of any residual uncomplexed material; and
   (d) eluting said specific antibody from said immunoadsorbent with an elution buffer capable of dissociating the complex of said specific antibody with said antigen moiety without effecting release of said antigen moiety from said carrier surface or destruction of the integrity of the eluted antibody.

2. The method of claim 1, wherein said antibody preparation is immune serum globulin.

3. The method of claim 1, wherein said complexing buffer is phosphate buffered saline, pH 7–7.2.

4. The method of claim 1, wherein said eluting of said antibody from said immunoadsorbent is effected with a low pH elution buffer; and prior to its being contacted with said antibody solution, said immunoadsorbent is subjected to a pretreatment comprising a first prewash with a buffer of lower pH than said elution buffer, and a subsequent prewash with said complexing buffer.

5. The method of claim 1, wherein said eluting of said antibody from said immunoadsorbent is effected with an elution buffer of high chaotropic ion concentration; and prior to its being contacted with said antibody solution, said immunoadsorbent is subjected to a pretreatment comprising a first prewash with a buffer of higher chaotropic ion concentration than said elution buffer, and a subsequent prewash with said complexing buffer.

6. The method of claim 1, wherein said antigen moiety of said immunoadsorbent is hepatitis B surface antigen.

7. The method of claim 6, wherein said antibody preparation is immune serum globulin.

8. The method of claim 6, wherein said porous glass carrier has an average pore diameter of about 150 nm.

9. The method of claim 6, wherein said elution buffer is selected from the group consisting of glycine-HCl buffer, pH 2.8; citrate-HCl buffer, pH 2.8; 4 M sodium thiocyanate; and 4 M potassium bromide.

10. The method of claim 9, wherein said elution buffer is 0.1 M citrate-HCl buffer, pH 2.8; and said immunoadsorbent is subjected to a pretreatment comprising a first prewash with 0.1 M citrate-HCl buffer, pH 2.5, and a subsequent prewash with said complexing buffer.

11. The method of claim 9, wherein said elution buffer is 4 M potassium bromide; and prior to its being contacted with said antibody solution, said immunoadsorbent is subjected to a pretreatment comprising a first prewash with 4.5 M potassium bromide, and a subsequent prewash with said complexing buffer.

* * * * *